United States Patent [19]

Matson et al.

[11] Patent Number: 5,429,807

[45] Date of Patent: Jul. 4, 1995

[54] METHOD AND APPARATUS FOR CREATING BIOPOLYMER ARRAYS ON A SOLID SUPPORT SURFACE

[75] Inventors: Robert S. Matson, Orange; Peter J. Coassin, San Juan Capistrano; Jang B. Rampal, Yorba Linda, all of Calif.; Edwin M. Southern, Kidlington, England

[73] Assignee: Beckman Instruments, Inc., Fullerton, Calif.

[21] Appl. No.: 144,954

[22] Filed: Oct. 28, 1993

[51] Int. Cl.⁶ .................... C08F 2/00; B01L 11/00; G05B 17/00; G01N 33/543
[52] U.S. Cl. .................... 422/131; 422/101; 422/102; 422/116; 435/6; 435/287; 436/518; 935/88
[58] Field of Search ............... 422/101, 102, 116, 131, 422/134, 132, 133, 135; 435/6, 287, 289, 299, 300, 301; 436/518; 935/88

[56] References Cited

U.S. PATENT DOCUMENTS

| | | | |
|---|---|---|---|
| 4,598,049 | 7/1986 | Zelinka et al. | 435/287 |
| 4,728,502 | 3/1988 | Hamill | 422/116 |
| 4,828,801 | 5/1989 | Lombardy et al. | 422/102 |
| 4,834,946 | 5/1989 | Levin | 422/101 |
| 4,882,127 | 11/1989 | Rosenthal et al. | 422/50 |
| 4,923,901 | 5/1990 | Koester et al. | 521/53 |
| 5,039,493 | 8/1991 | Oprandy | 422/101 |
| 5,112,736 | 5/1992 | Caldwell et al. | 435/6 |
| 5,143,854 | 9/1992 | Pirrung et al. | 436/518 |

FOREIGN PATENT DOCUMENTS

WO89/10977  11/1989  European Pat. Off. .
93/09668  5/1993  WIPO .

OTHER PUBLICATIONS

Southern, E. M. et al.; "Analyzing and Comparing Nucleic Acid Sequences by Hybridization to Arrays of Oligonucleotides; Evaluation Using Experimental Models"; Genomics 13, No. 4. pp. 1008-1017; Aug., 1992.

Primary Examiner—Robert J. Warden
Assistant Examiner—Christopher Y. Kim
Attorney, Agent, or Firm—William H. May; P. R. Harder; Janis C. Henry

[57] ABSTRACT

An automated method and apparatus for performing biopolymer synthesis on a two-dimensional support surface whereby a two-dimensional matrix or array of biopolymers are obtained on the surface. An applicator in the form of a thick plate having in a surface at least one cavity in the form of an open chamber or channel is used for applying reagents to the surface of a solid phase support material. The applicator is positioned over the solid support material with the surface having the cavity sealed against the material surface. For each cavity, reagents for synthesis are introduced sequentially into one end of the cavity and collected from the other end of the cavity. A one-dimensional array of biopolymers are thus formed on the support material, where each element of the array contains a population of biopolymers having identical sequence. Further synthesis of additional biopolymers is performed by linearly moving or rotating the applicator relative to the support material and carrying out synthesis procedure so that another one-dimensional matrix or array of biopolymers are formed at an offset position to the previous array. At each overlapping region of the two arrays, a cell of biopolymers are formed which each comprises a strand from the first array and a strand from the second array. The result is a two-dimensional array of biopolymers of different sequences at each discrete cell. The arrays of discrete cell containing different biopolymers may be used to conduct hybridization reaction analysis of a biological sample.

21 Claims, 7 Drawing Sheets

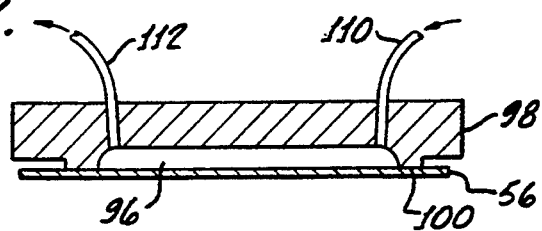
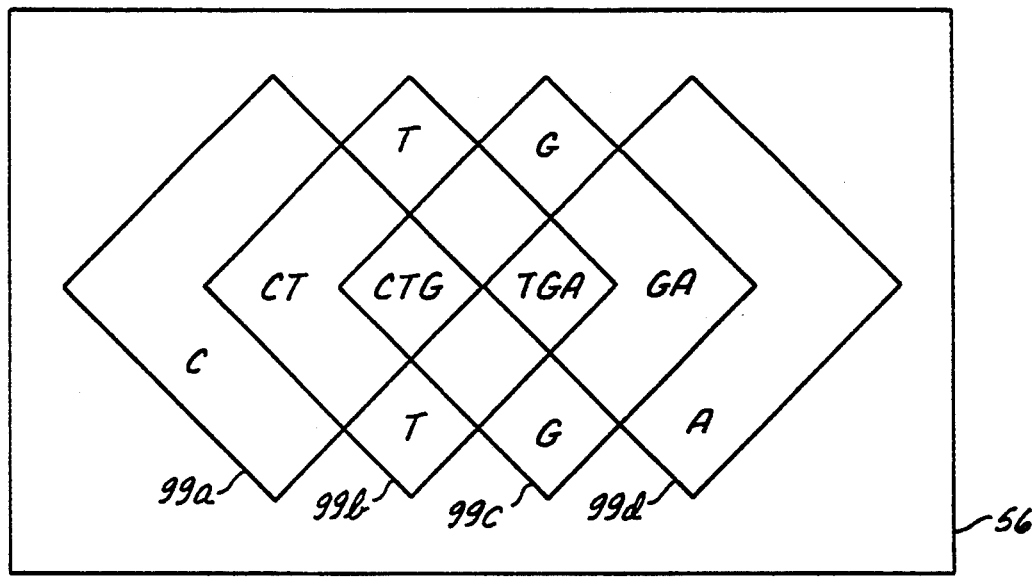
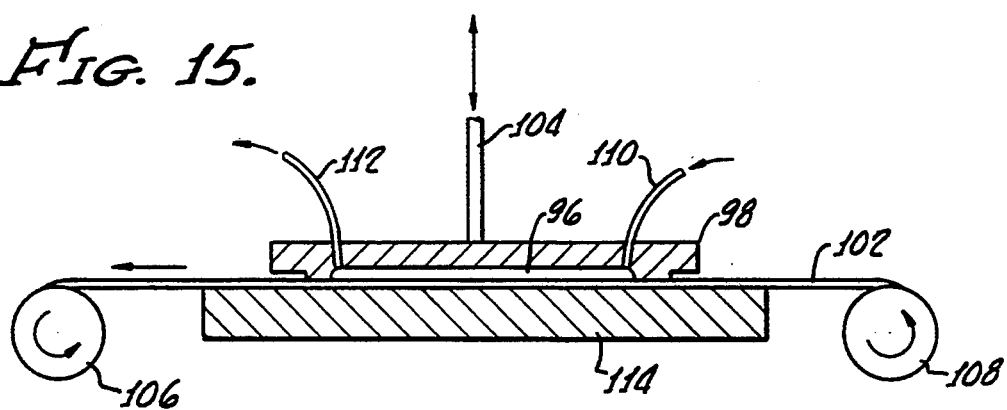

METHOD AND APPARATUS FOR CREATING BIOPOLYMER ARRAYS ON A SOLID SUPPORT SURFACE

BACKGROUND OF THE INVENTION

1. Field of the Invention

The present invention relates to synthesis of biopolymers on a solid support surface, and analysis by hybridization reaction.

2. Description of Related Art

Biopolymers synthesis has been widely practiced by using solid phase substrates. One form of biopolymer synthesis is the synthesis of deoxyribonucleic acid ("DNA") which can be performed on a particulate solid phase support in a reaction column. The process can be automated in which the relevant reagents are delivered to the reaction column under the control of a microprocessor. An example of such automated DNA synthesis instrument is the Oligo 1000 DNA Synthesizer developed and sold by Beckman Instruments, Inc. A description of this instrument may be found in copending U.S. Pat. application Ser. Nos. 07/936,976 and 07/909,232 which have been assigned to the assignee of the present application. The synthesized DNA strand is cleaved from the solid support in the column and collected for further processing or use.

DNA synthesis has also been performed using a flat sheet of solid phase support material. In international patent publication No. WO 89/10977, it disclosed that DNA can be synthesized onto a glass slide to form a structured one-dimensional matrix or array of polynucleotides. The synthesized material is left attached to the glass slide which is then applied in a hybridization reaction process for sequence analysis of unknown polynucleotide sequences. The process and apparatus disclosed require extensive manual steps.

SUMMARY OF THE INVENTION

The present invention is directed to a method and apparatus for performing biopolymer synthesis on a support surface whereby a two-dimensional matrix or array of biopolymers are obtained on the surface.

In one embodiment of the present invention, an applicator in the form of a thick plate having in a surface a plurality of parallel open channels is used for applying reagents to the surface of a solid phase support material. The applicator is positioned over the solid support material with the surface having the channels sealed against the material surface. For each channel, reagents for synthesis are introduced sequentially into one end of the channel and collected from the other end of the channel. Biopolymers are synthesized on the surface of the material that is exposed to the reagents flowing through the open channel, having a specific sequence which depends on the particular sequence of reagents supplied to the particular channel. A parallel one-dimensional array of biopolymers are thus formed on the support material, where each element of the array contains a population of biopolymers having identical sequence. The different channels may correspond to different biopolymer sequences by distributing reagents accordingly to the different channels using an appropriate reagent distribution system.

After synthesis, the biopolymers may be cleaved from the solid support material and collected for further processing and/or analysis. It may also be desirable to further synthesize additional biopolymers by rotating the applicator with respect to the solid support material and carrying out synthesis procedure so that another parallel one-dimensional matrix or array of biopolymers are formed at an angle to the previous array. At each overlapping region of the two parallel arrays, a cell of biopolymers are formed which each comprises a strand from the second array serially connected to a strand from the first array. The result is a two-dimensional array of biopolymers of different sequences at each discrete cell. Further rotation of the applicator and conducting further synthesis may be carried out as desired to build up longer biopolymers or specific arrays of various combinations of biopolymers. The arrays of discrete cell containing different biopolymers may be used to conduct hybridization reaction analysis of a biological sample.

In another embodiment of the present invention, instead of parallel linear channels, the applicator used for synthesis may be provided with one or more curvilinear channels. When the applicator is positionally offset between synthesis, biopolymers are synthesized at a two-dimensional array of cells of a specific configuration. In a further embodiment, instead of channels, a two-dimensional open chamber may be provided in one surface of the applicator. When incrementally offsetting the relative position of the applicator and support material between synthesis, biopolymers are synthesized onto overlapping areas of the solid support surface, whereby different overlapping regions have different sequences of synthesized biopolymers. The chamber may have an opening having a specific planar geometry that is designed to obtain specific two-dimensional array of overlapping regions with the appropriate incremental positioning.

The above-described processes may be automated.

BRIEF DESCRIPTION OF THE DRAWINGS

FIG. 12 is a sectional view taken along line 11—12 in FIG. 11.

FIG. 13 is a planar view of a sheet of solid support material schematically illustrating a two-dimensional array of cells of synthesized biopolymers.

FIG. 15 is a schematic illustration of a device for manipulating the applicator to obtain the arrays illustrated in FIGS. 13 and 14.

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

While the following description refers to oligonucleotide (or DNA) synthesis as an example of a type of biopolymer synthesis that can be carried out in accordance with the principles of the present invention, but it is understood that the present invention is not limited to such form of synthesis. The present invention is applicable generally to other types of biopolymer synthesis without departing from the scope and spirit of the present invention.

Figure 1:
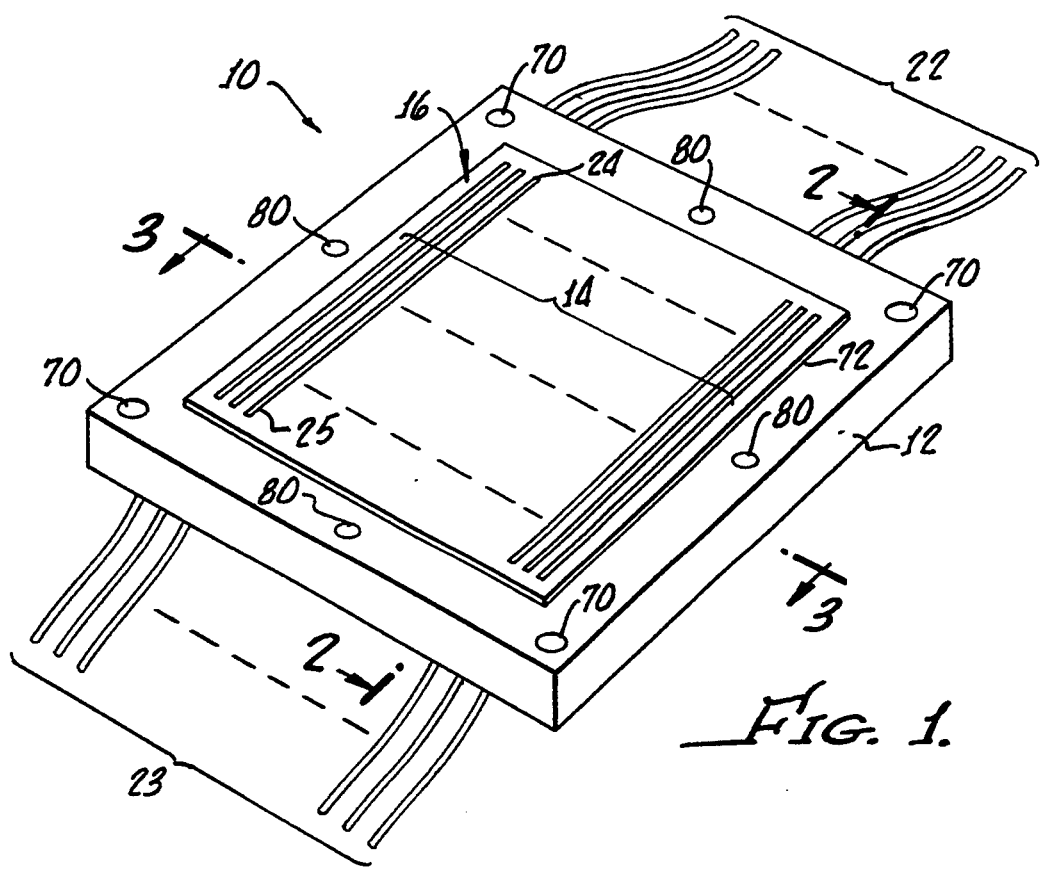
FIG. 1 is a perspective view of a reagent applicator in accordance with one embodiment of the present invention.
Figure 2:
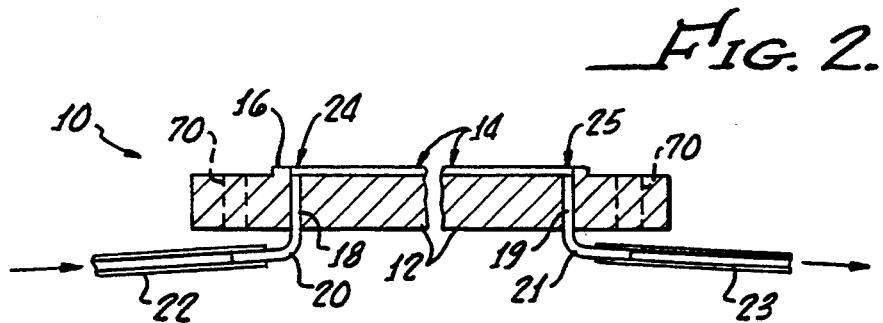
FIG. 2 is a sectional view taken along line 2—2 in FIG. 1.
Figure 3:
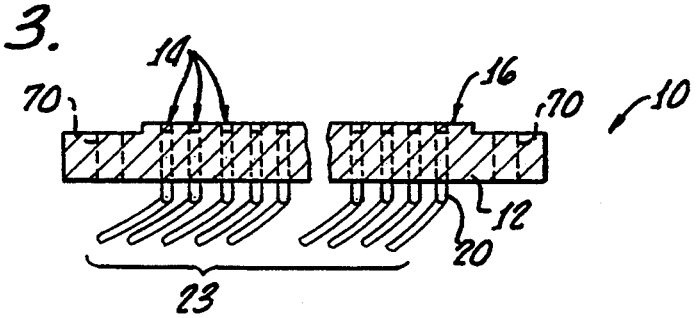
FIG. 3 is a sectional view taken along line 3—3 in FIG. 1.

Referring to FIGS. 1-3, an applicator 10 for application of reagents to perform oligonucleotide synthesis on a sheet of material is shown. The prototype applicator 10 is illustrated to be in the form of a thick rectangular block or plate 12, but it may take on other geometrical shapes. The plate 12 is made of aluminum for ease of machining, but can be made of other materials which are inert to the chemical reagents involved in the particular synthesis process for which the applicator 10 is used.

A plurality of parallel open channels 14 are provided in one plate surface 16. In the illustrated prototype, there are 64 slender channels 14, each 500 μm wide, 0.8 mm deep, 62 mm long, and at 0.8 mm centerline spacing between channels 14. These channels 14 were machined by using a disc saw having the appropriate thickness. At either end (input end 24 and output end 25) of each channel 14, a hole (18, 19) is drilled through the plate 12 which communicates to a short length of tubing connector (20, 21). A teflon tubing (22, 23) is connected to each connector (20, 21). The tubings 22 are for feeding reagents to the input ends 24 of the channels 14 and the tubings 23 are for draining reagents from the channels 14 from the output ends 25.

Figure 4:
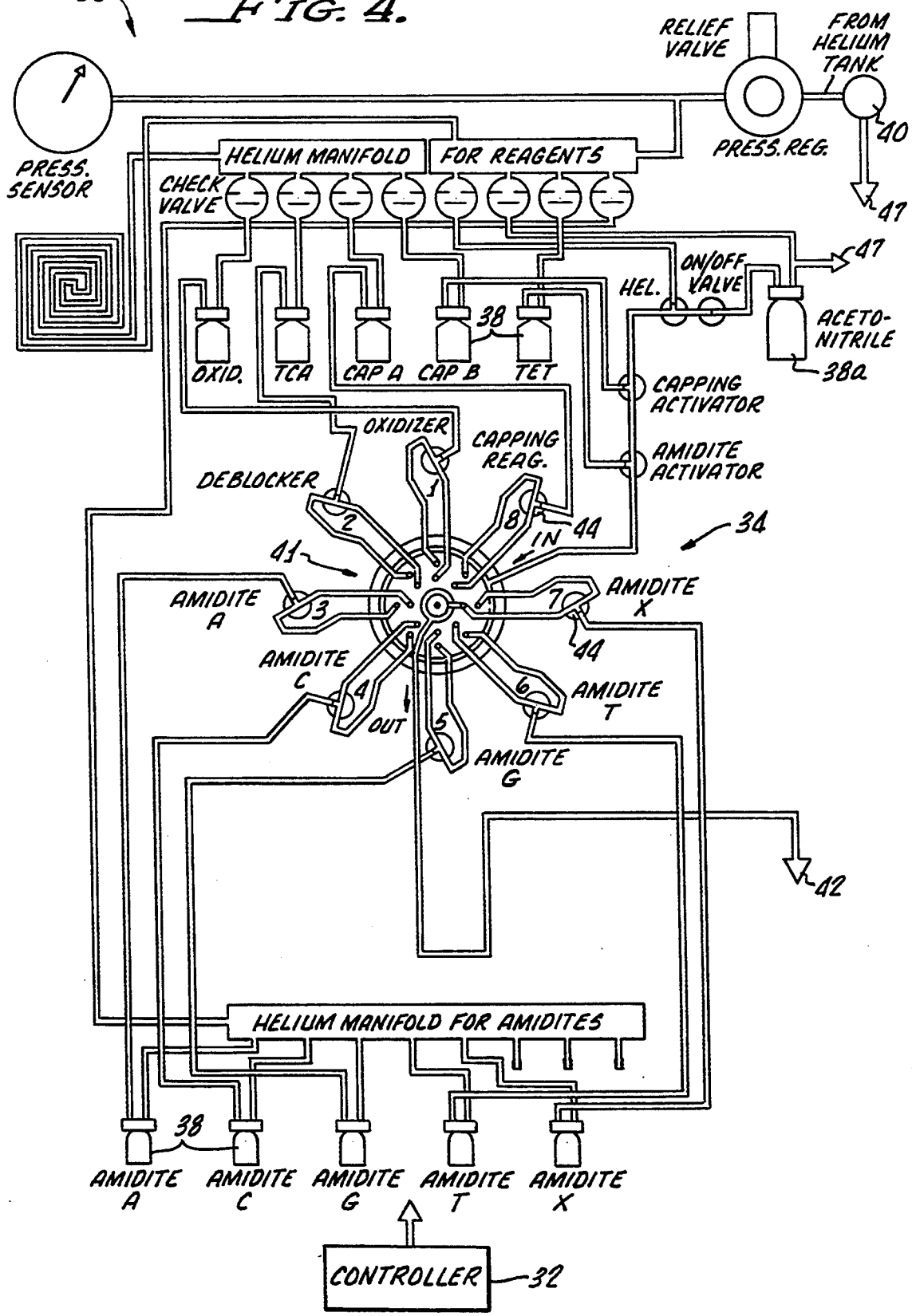
FIG. 4 is a schematic drawing of the reagent dispensing section of the reagent distribution device in accordance with one embodiment of the present invention.
Figure 5:
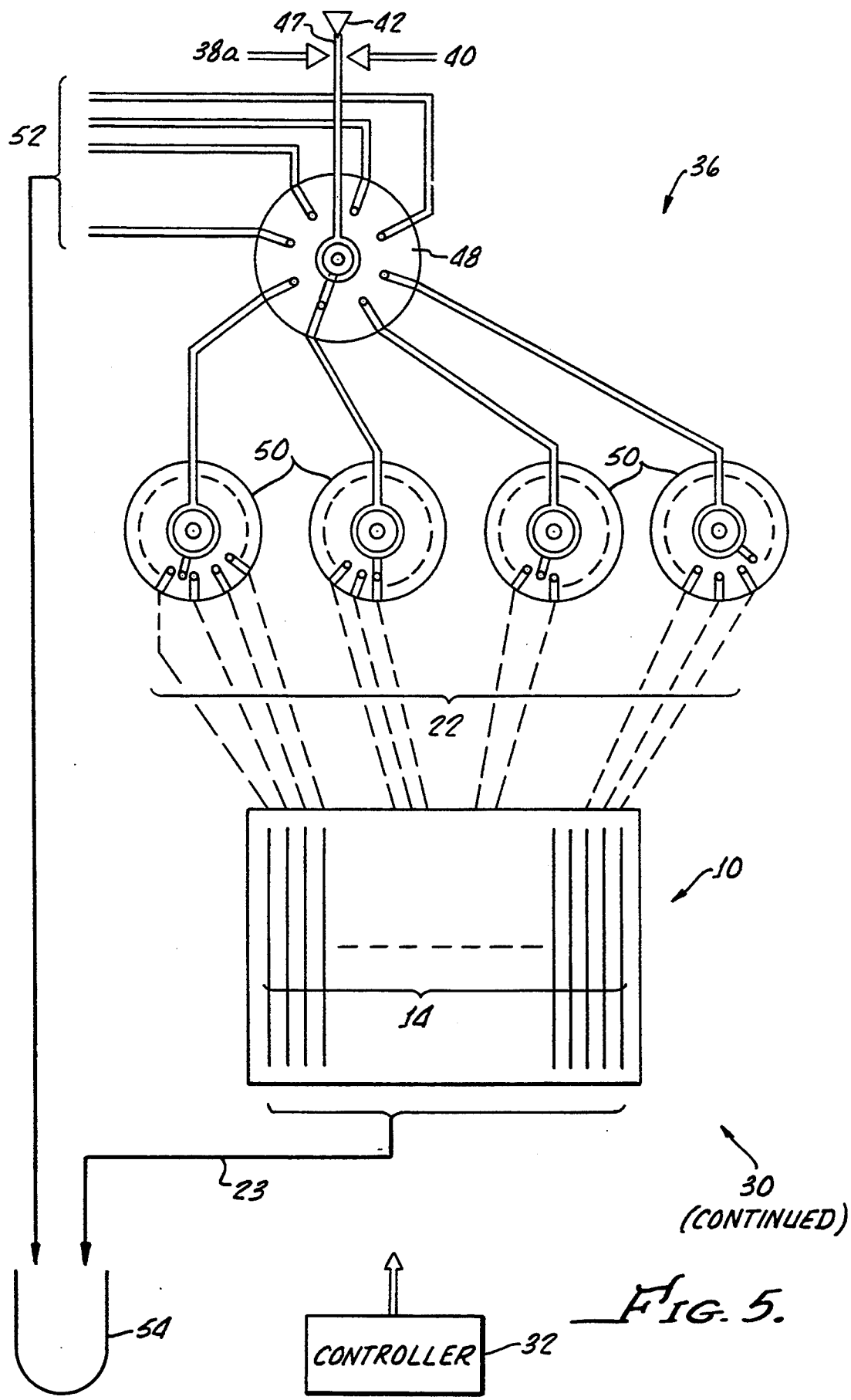
FIG. 5 is a schematic drawing of the reagent distribution section of the reagent distribution device in accordance with one embodiment of the present invention.

The tubings 22 are coupled to a reagent distribution device for feeding the appropriate reagents for DNA synthesis. An example of an automated device 30 is schematically illustrated in FIGS. 4 and 5. This device 30 operates under the control of a microprocessor based controller 32. It comprises essentially a reagent dispensing section 34 (FIG. 4) and a reagent distribution section 36 (FIG. 5). The reagent dispensing section 34 selectively dispenses the appropriate reagents in a programmed sequence from the reagent containers 38 by applying a pressure using an inert gas source 40, and delivers the reagents under pressure to an output 42 of this section 36. From this point on, the distribution section 34 selectively distributes the reagents to the tubings 22.

The reagent dispensing section 34 is essentially similar to the device disclosed in U.S. patent application Ser. Nos. 07/936,976 and 07/909,232 which have been commonly assigned to the assignee of the present invention and are incorporated by reference herein. This device implements a multi-port rotary valve 41 and a number of isolation valves 44 controlled by the controller 32 to accomplish a low-dead volume, non-cross contaminating configuration for delivering reagents to the output 42. The details of this device can be obtained from the above patent documents and will not be described herein. (In fact, other automated synthesis systems may be modified to accomplish reagent dispensing.) In the present invention, instead of a single reaction column for DNA synthesis as in the device described in the above patent documents, it is replaced by the reagent distribution section 36 described herein below and the applicator 10, which in combination may be viewed as a multiple column synthesis system. The reagents delivered to the output 42 by the reagent dispensing section 34 are distributed by the distribution section to the individual columns (channels 14) to carried out synthesis in each column (channel 14).

More specifically, the reagents from the output 42 of the reagent dispensing section 34 are selectively passed through a main 8-port rotary valve 48 and its four branch 16-port rotary valves 50 as schematically illustrated in FIG. 5. Each of the valves 48 and 50 can deliver reagents through a selected one of the output ports. This configuration results in 64 selectable outputs from the reagent distribution section 36 (four ports 52 of the main valve 50 being used for purging reagents to a waste container 54). These 64 outputs are connected by the tubings 22 to the input connectors 20 of the applicator 10 where DNA synthesis is to take place. The output connectors 21 are connected by tubings 23 to the waste container 54. To facilitate flushing the reagent distribution section 36 with acetonitrile buffer and purging the reagent distribution section 36 with helium, the acetonitrile source 40 and acetonitrile container 38a connected to the upstream of the distribution section 36 via a control valve 47. The valve 47 is controlled to selectively release acetonitrile or helium into the distribution section 36 without having to run the acetonitrile and helium through the reagent dispensing section 34.

More particularly, a particular reagent from the output 42 of the reagent dispensing section 34 is delivered under pressure through a selected output port in the main valve 48 to its associated branch valve 50 through a selected output port to its associated channel 14 in the applicator 10. By coordinating the operations of the main and branch valves 48 and 50 with the controller 32, specific reagents are selectively delivered to the various channels 14 in specific sequences.

Figure 6:
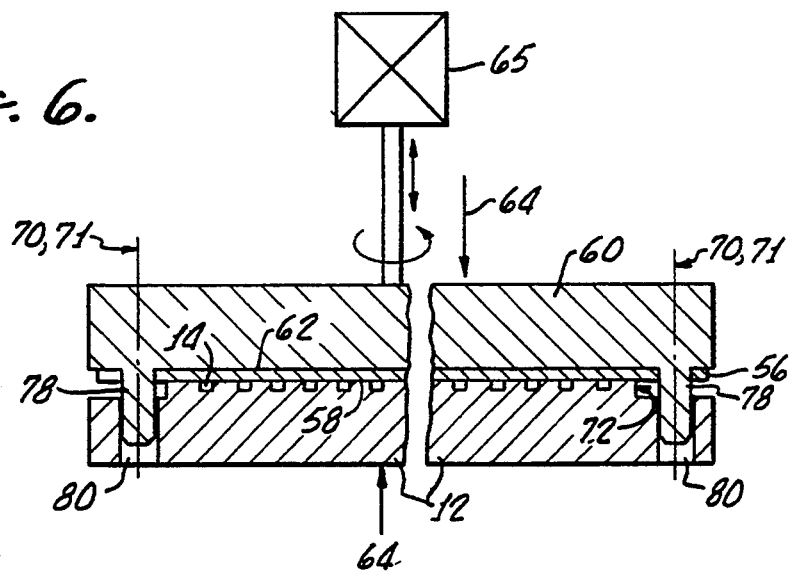
FIG. 6 is a sectional view of the reagent applicator in operation with a sheet of solid support material.

Referring to FIG. 6, the applicator 10 is to be applied for DNA synthesis onto a flat surface of a solid support material. In the illustrated example, the material is a 25 μm thick pliant sheet 56 of polypropylene. Other materials may be suitable, such as glass sheets. To allow monomer binding onto the sheet 56, the polypropylene is appropriately derivatized (e.g. animated) which can withstand the conditions of DNA synthesis, either prior to or during application of the applicator 10 in the manner described herein below. The chemistries for the derivatization of polypropylene for DNA synthesis has been described in copending U.S. patent application Ser. No. 07/091,100, which has been assigned to the assignee of the present application and is herein incorporated by reference, and for the derivatization of glass is disclosed in, for example, international patent application publication WO 89/10977.

In operation, the polypropylene sheet 56 is positioned over the plate 12, with the derivatized surface 58 sealed against the surface of the plate 12 having the open channels 14. The pliancy of the sheet 56 facilitates sealing of the channels without requiring any additional sealing material. A suitable stiff backing plate 60 is laid on the other surface 62 of the sheet 56 and a force 64 is applied on the back of the plates 60 and 12 to sandwich the sheet 56, for example, by simply clamping the plates 12 and 60. Alternatively, the plates 60 and 12 may be bolted together by bolts and nuts through holes 70 and 71 at the periphery of the plates 12 and 60. It is noted that a shoulder 72 is milled around the periphery of plate 12 outside of the channels 14 such that the surface 16 having the channels 14 is raised above the periphery of the plate 12. This reduces the area of the contact surface 16 of the plate 12 to a minimum necessary to form the channels 14 so as to increase the sealing pressure from the applied force 64 while allowing sufficient peripheral structure to allow for bolting the plates 12 and 60.

To perform DNA synthesis process, for each cycle of synthesis, appropriate reagents (including acetonitrile buffer, phosphoramidites, oxidization reagent, capping reagents activator, deblocker, etc.) are fed sequentially (under pressure from an inert gas, e.g. helium), in accordance with the conventional chemistry requirements for DNA synthesis, into the input end 24 of each channel 14. The reagents flow through the channels 14 and come into contact with the exposed parallel sections of the sheet 56 where chemical reactions associated with synthesis take place. Reagents flow out or is purged through the output ends 25 of the channels 14 and are collected in the waste container 54. For each cycle of synthesis, a DNA monomer building block (one of the bases A, C, G and T which correspond to the amidites used) is synthesized to a building block which has been synthesized in the previous cycle, the first building block being attached to the derivatized sheet. DNA strands of specific lengths and oligonucleotide sequences are thus synthesized to the surface 58 of the sheet 56 and extend from the sheet 56 after a desired number of cycles. The sequence obtained depends on the sequence of amidires (monomers) applied for the synthesis cycles. It is noted that if the sheet 56 has not been derivatized prior to placing on the applicator plate 12, the sheet 56 can be derivatized using the applicator 10 by applying appropriate derivatizing reagents to the channels 14 prior to beginning synthesis cycles.

It can be appreciated that by controlling the operation of the valves 42, 48 and 50 in the reagent dispensing section 34 and the reagent distribution section 36, any of the reagents may be delivered from the containers 38 to the output 42 of the reagent dispensing section and then delivered to a desired channel 14. Thus, the channels 14 can be used to synthesis polynucleotides of lengths and sequences different from one another.

Figure 7:
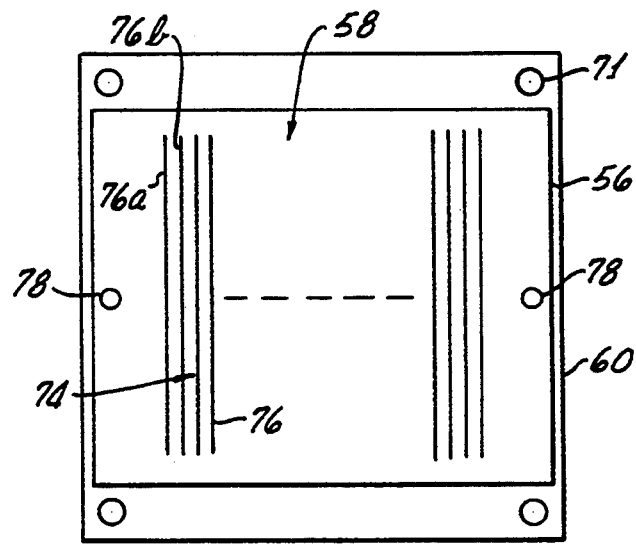
FIG. 7 is a planar view of the sheet of solid support material schematically illustrating a parallel one-dimensional array of biopolymers synthesized thereon.

Referring to FIG. 7, the end result is a parallel one-dimensional (M×1) matrix or array 74 of polynucleotide strands formed on the derivatized surface 58 of the sheet 56, each element 76 of the array being in the shape of a longitudinal narrow band having a width substantially equal to that of the channels 14 in the plate 12 and containing strands of polynucleotides of identical sequence along the same band. It is noted that the term "dimension" used herein does not refer to the physical size and shape of the array or matrix. Rather it refers to the direction of the ordered arrangement of the discrete array elements. Therefore, one-dimensional (M×1) array refers to an array having discrete elements arranged in a single direction irrespective of the size of the individual elements; and two-dimensional array refers to an array having discrete elements arranged in two directions, e.g. a M×N matrix, or an irregular matrix of discrete elements distributed over an area.

After the above synthesis process, the polynucleotide strands may be cleaved from the sheet and collected for further processing. The appropriate cleaving reagents are applied to each of the channels 14 to mobilize the attached strands from the sheet and the output tubings 23 from the applicator 10 should therefore be connected to appropriate containers for collection of the cleaved strands.

Figure 8:
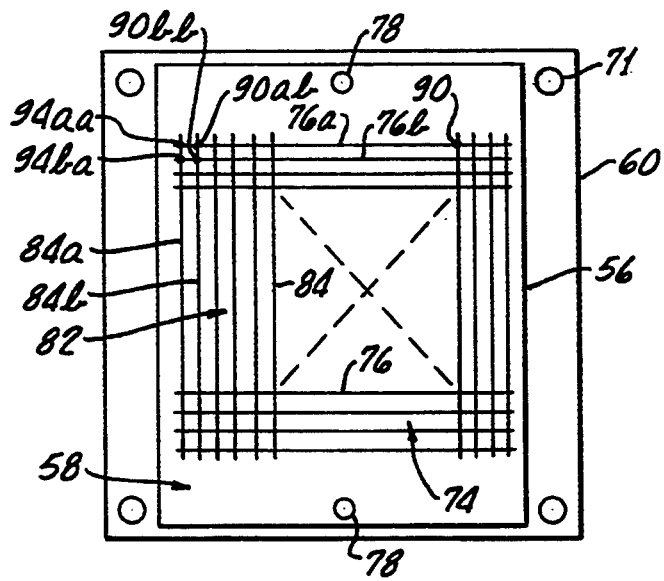
FIG. 8 is a planar view of the sheet of solid support material schematically illustrating the synthesis of another parallel one-dimensional array of biopolymers to result in a two-dimensional array of cells of synthesized biopolymers at the overlapping regions of the two arrays.

Instead of cleaving the strands from the sheet 56, it may be desirable to further synthesize additional polynucleotides on the sheet by rotating the applicator 10 by an angle (90° in the example illustrated herein) with respect to the sheet 56 as supported by the backing plate and carrying out synthesis procedure as before so that a second parallel one-dimensional array 82 (having elements or bands 84) of polynucleotides are formed orthogonal to the previous array (see FIG. 8). The channels 14 are purged with helium gas from the reagent distribution device 30 before lifting and rotating the plate 60. Indexing pins 78 are provided on the plate 60 and holes 80 are provided on the plate 12 to facilitate indexing the rotated position of the plate 12 with reference to the backing plate 60. The indexing pin 78 extends through the edge of the sheet 56 to maintain its orientation with respect to the plate 60. The above movement of the plate 60 may be automated by an actuator 65 schematically illustrated in FIG. 6.

At each overlapping region of the two parallel arrays 74 and 82, there is a discrete cell 90 in which each overall polynucleotide strand includes a strand from the second array 82 serially connected to a strand from the first array 74. Thus, it can be appreciated that while each strand along the same band (76, 84) in an array (74, 82) is the same, the overall strands are different between cells. To illustrate this point, let the bands 76a, 76b in array 74 and bands 84a and 84b in the array 82 contain polynucleotides which have the following sequences (the left most nucleotide is attached to the sheet 56):

band 76a=ACT
band 76b=CGTA
band 84a=TGAA
band 84b=ATG

Then the overall polynucleotide strands in cells 90aa, 90bb, 90ab and 90ba has the following sequences:

cell 90aa=ACTTGAA
cell 90bb=CGTAATG
cell 90ab=ACTATG
cell 90ba=CGTATGAA

In the illustrated example, there would be a two-dimensional 64×64 cells 90 configured in a two-dimensional (M×N) matrix or array. Further rotation and/or translation of the applicator plate 12 with respect to the backing plate 60 and conducting further synthesis may be carried out as desired to build up longer strands or obtain an array of a combination of strands of different sequences. It is noted that different applicators may be used for the two arrays. The applicators may have channels of different width, spacing and geometry.

Figure 9:
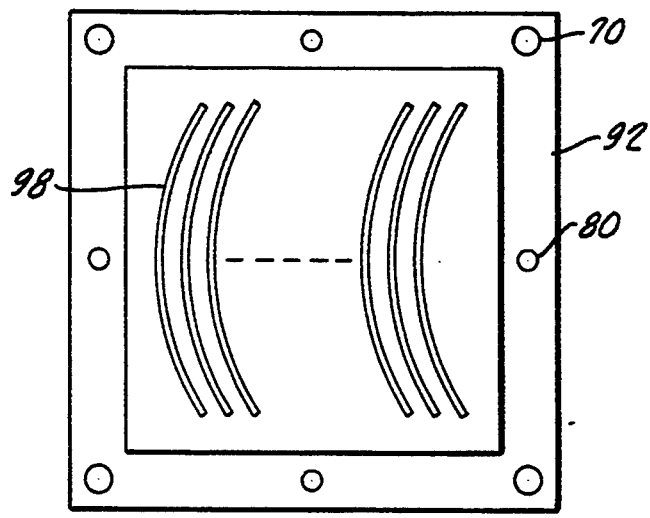
FIG. 9 is a planar view of the open channels in one surface of an applicator in accordance with another embodiment of the present invention.
Figure 10:
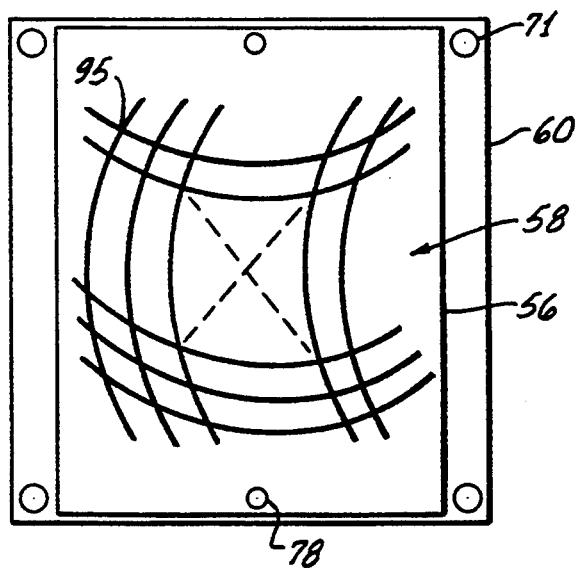
FIG. 10 is a planar view of the sheet of solid support material schematically illustrating another configuration of a two-dimensional array of synthesized biopolymer array obtained using the applicator in FIG. 9.

In another embodiment of the present invention as shown in FIG. 9, instead of parallel slender channels 14 on the surface 16 of the plate 12, the applicator 92 used for synthesis may be provided with one or more curvilinear channels 94. When the applicator 92 is rotated by 90° with respect to the sheet 56 between synthesis, biopolymers are synthesized on the sheet 56 at a two-dimensional array of cells 95 of the specific configuration as shown in FIG. 10.

Figure 11:
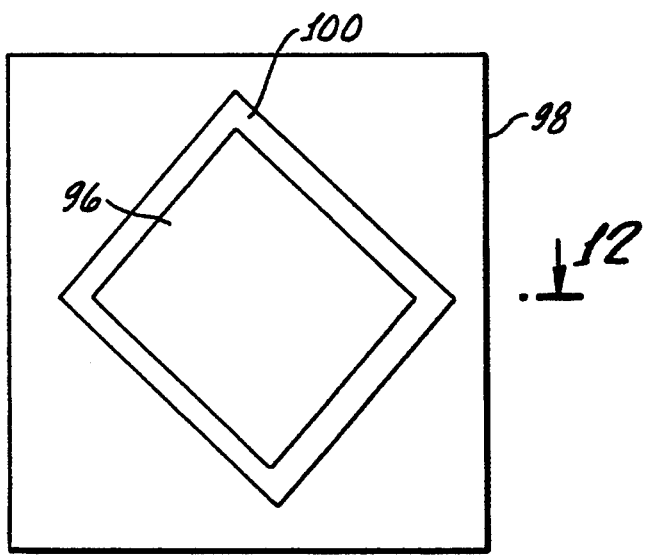
FIG. 11 is a planar view of an open chamber in one surface of an applicator in accordance with a further embodiment of the present invention.
Figure 14A:
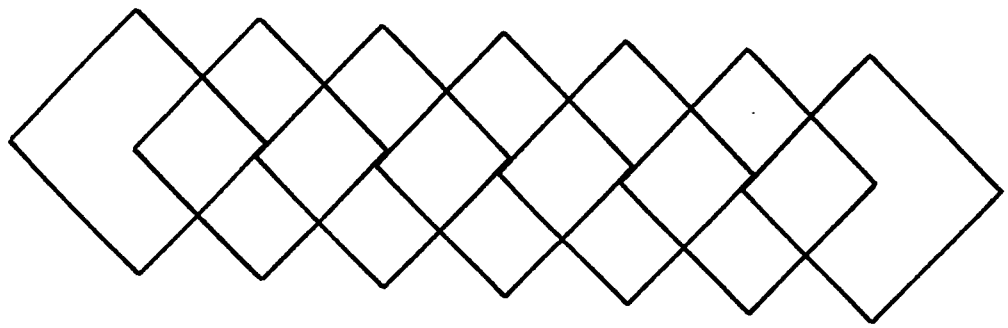
FIGS. 14A-D schematically illustrate other possible configurations of two-dimensional array of cells of synthesized biopolymers.
Figure 14B:
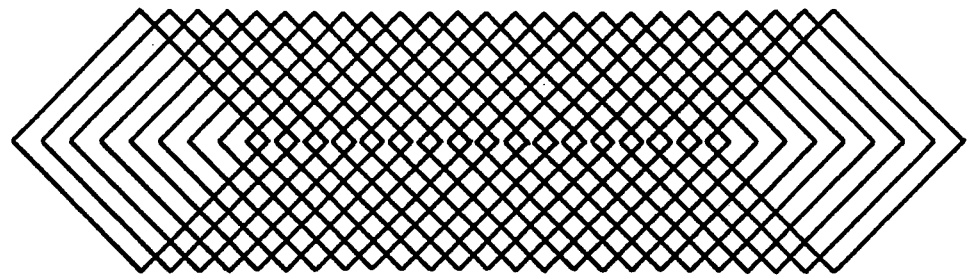
Figure 14C:
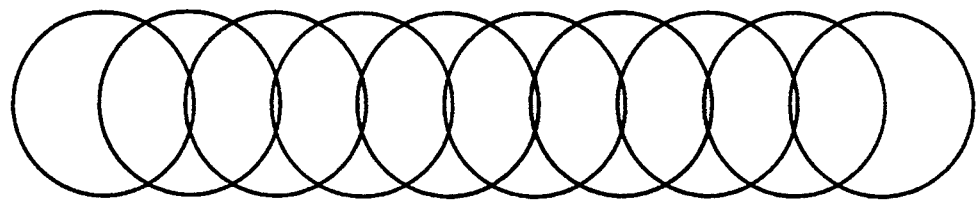
Figure 14D:
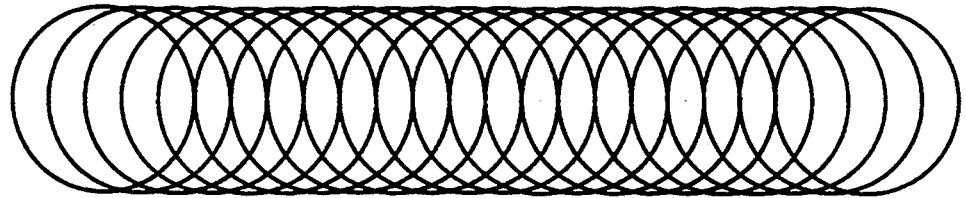

In a further embodiment as shown in FIGS. 11 and 12, instead of channels, a two-dimensional open chamber 96 may be provided in one surface 100 of the applicator 98. Referring to FIG. 13, when synthesis is carried out by incrementally advancing the position of the applicator 98 with respect to the sheet 56 between synthesis, biopolymers are synthesized into regions 99a–d (in that order) with overlapping regions, whereby different overlapping regions have different sequences of synthesized biopolymers. Given that region 99a–d contain polynucleotides having the following sequences (for simplicity, a single oligomer is illustrated; polynucleotides share the same principle):

99a = C
99b = T
99c = G
99d = A

Then the result is a two-dimensional array of discrete cells containing the specific sequences illustrated in FIG. 13. The chamber may have a specific planar geometry of its opening, e.g. circle or square, designed to obtain specific two-dimensional arrays of overlapping regions of biopolymers with the appropriate incremental positioning (see examples illustrated FIGS. 14A–D).

FIG. 15 shows a schematic arrangement of a "scanning" array device in which a derivatized sheet 102 is linearly translated. The applicator 98 is fixed in a lateral position, but is support to move vertically by means of the shaft 104. The sheet 102 is in a form of a belt wound between rollers 106 and 108. To perform synthesis, the shaft 104 is lowered and pressed on the sheet 102. Synthesis reagents are introduced into the chamber 96 through the tubing 110 and removed from the chamber 96 through the tubing 112. A reagent distribution device (not shown) having a reagent dispensing section as shown in FIG. 4 may be used. After a specific number of synthesis cycles, the shaft 104 is lifted and the roller 106 is rotated to wind the sheet 102 so as to incrementally move it laterally between the applicator 98 and the support plate 114 by a specific distance. The shaft 104 is lowered to conduct further synthesis, thereby obtaining an overlapping array pattern such as those illustrated in FIGS. 13 and 14. In a fully automated device, motors (not shown) are provided to actuate the shaft 104 and rollers 106 and 108. The coordination of the actuation of the shaft 104 and rollers 106 and 108 can be controlled under the direction of the same controller 32 in coordination with the reagent dispensing function.

The above described arrays and variations thereof may be used to conduct hybridization reaction analysis of unknown polynucleotide in a DNA sample. Generally, two strands of polynucleotides hybridize under a condition when they have complementary bases. The basic principles of hybridization reaction sequencing may be found in International Patent Publication WO 89/10977. Hybridization reaction analysis can be done by deprotecting the polynucleotides on the sheet 56 using conventional chemistries, applying the sample across the array of cells and allowing hybridization reaction to take place. By observing the result of the hybridization reaction using, for example, fluorescence staining technique, one can determine the cell or cells within the array which hybridized with part or all of the sample. Since the sequence of the polynucleotide at each cell on the sheet is known, the identity or the sequence of the DNA sample can be determined by reconstruction from the known sequences at the cells where hybridization reaction took place. In the illustrated example, there are 64×64=4096 cells of potentially different hybridization sites which can provide a vast amount of information about the sample. One can build an applicator with a larger number of channels which would increase the resolving power of the analysis exponentially.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

We claim:

1. A device for synthesizing biopolymer comprising:
   a fixed polypropylene support having a surface activated for attaching bipolymers;
   an applicator for applying reagents to said activated surface, the applicator contacting said activated surface;
   positioning means for positioning the applicator with respect to the activated surface in first and second positions;
   reagent supply means for distributing reagents to said activated surface to synthesize a first one-dimensional array of biopolymers in said first position and a second one-dimensional array of biopolymers in said second position, the positioning means positioning the first and second positions such that said second one-dimensional array overlaps the first one-dimensional array to form a two-dimensional array of cells at overlapping regions on said surface in each of which a third biopolymer is obtained which includes corresponding biopolymer strands from said first and second arrays.

2. A device as in claim 1 wherein said applicator includes a face having therein at least one cavity for flowing reagents for synthesis of the biopolymer.

3. A device as in claim 2 wherein the means for positioning includes means for sealing said cavity against said activated surface and flowing reagents for synthesis through the cavity such as to contact the activated surface with the reagents to allow reactions associated with synthesis to take place.

4. A device as in claim 3 wherein the cavity has a circular opening.

5. A device as in claim 3 wherein the cavity is in the shape of an elongated channel.

6. A device as in claim 2 wherein said applicator includes a face having a plurality of elongated channels having one end communicated to the reagent supply means, whereby the first and second arrays of biopolymers synthesize along regions on the activated surface corresponding to said channels.

7. A device as in claim 1 wherein said applicator includes a face having a plurality of elongated channels having one end communicated to the reagent supply means whereby the first and second arrays of biopolymers synthesize along regions on the activated surface corresponding to said channels, and the positioning means includes means for rotating the applicator relative to the activated surface.

8. A device as in claim 7 wherein the positioning means rotates the applicator by 90° relative to the activated surface such that the second one-dimensional array is orthogonal to the first one-dimensional array.

9. A device as in claim 1 wherein the positioning means includes means for moving the applicator linearly relative to the activated surface.

10. A device as in claim 1 wherein the positioning means includes means for rotating the applicator relative to the activated surface.

11. A method for synthesizing biopolymer comprising the steps of:
providing a fixed polypropylene support having a surface activated for attaching biopolymers;
providing an applicator in contact with said activated surface for applying reagents to said activated surface;
positioning the applicator with respect to the activated surface and applying reagents to said activated surface to synthesize a first one-dimensional array of biopolymers;
repositioning the applicator and applying reagents to said activated surface to synthesize a second one-dimensional array of biopolymers in a manner where said second one-dimensional array overlaps the first one-dimensional array to form a two-dimensional array of cells at overlapping regions on the activated surface in each of which a third biopolymer is obtained which includes a corresponding biopolymer from said first and second arrays of biopolymers.

12. A method as in claim 11 wherein said applicator provided includes a face having therein at least one cavity for flowing reagents for synthesis of the biopolymer, and the positioning and repositioning steps include the steps of:
sealing said cavity against said activated surface; and
flowing reagents for synthesis through the cavity such as to contact the activated surface with the reagents to allow reactions associated with synthesis to take place.

13. A method as in claim 12 wherein the cavity has a circular opening.

14. A method as in claim 12 wherein the cavity is in the shape of an elongated channel.

15. A method as in claim 12 wherein said applicator includes a face having a plurality of elongated channels having one end communicated to the reagent supply means, whereby the first and second arrays of biopolymers synthesize along regions on the activated surface corresponding to said channels.

16. A method as in claim 11 wherein said applicator includes a face having a plurality of elongated channels having one end communicated to the reagent supply means whereby the first and second arrays of biopolymers synthesize along regions on the activated surface corresponding to said channels, and the positioning step includes the step of rotating the applicator relative to the activated surface.

17. A method as in claim 16 wherein the applicator is rotated by 90° relative to the activated surface such that the second one-dimensional array is orthogonal to the first one-dimensional array.

18. A method as in claim 11 wherein the positioning step includes the step of moving the applicator linearly relative to the activated surface.

19. A method as in claim 11 wherein the positioning step includes the step of rotating the applicator relative to the activated surface.

20. A method for synthesizing polynucleotides comprising the steps of:
providing a fixed polypropylene support having a surface activated for attaching polynucleotides;
providing an applicator in contact with said activated surface for applying reagents suitable for polynucleotide synthesis to said activated surface;
positioning the applicator with respect to the activated surface and applying reagents to said activated surface to synthesize a first one-dimensional array of polynucleotides;
repositioning the applicator and applying reagents to said activated surface to synthesize a second one-dimensional array of polynucleotides in a manner where said second one-dimensional array overlaps the first one-dimensional array to form a two-dimensional array of cells at overlapping regions on the activated surface in each of which a third polynucleotide is obtained which includes corresponding polynucleotide strands from said first and second arrays.

21. A device for synthesizing biopolymer comprising:
a support material having a surface activated for attaching biopolymers;
an applicator for applying reagents to said activated surface, the applicator contacting said activated surface;
reagent supply means for distributing reagents to said activated surface to synthesize a first one-dimensional array of biopolymers in a first position and a second one-dimensional array of biopolymers in a second position, the reagent supply means including:
a primary rotary valve with a plurality of ports,
a plurality of secondary rotary valves each with a plurality of ports, each secondary rotary valve connected in parallel with respect to the other secondary rotary valves and the primary and secondary rotary valves connected in series, the ports of the primary and secondary rotary valves being capable of variable alignment, and
a controller for selective operation of the primary and secondary rotary valves resulting in selective reagent distribution to the applicator in a sequence-specific manner, and
positioning means for positioning the applicator with respect to the activated surface in the first and the second positions, the positioning means positioning the first and second positions such that said second one-dimensional array overlaps the first one-dimensional array to form a two-dimensional array of cells at overlapping regions on said surface in each of which a third biopolymer is obtained which includes corresponding biopolymer strands from said first and second arrays.

* * * * *